United States Patent [19]

Schmidt et al.

[11] Patent Number: 5,679,439

[45] Date of Patent: Oct. 21, 1997

[54] HEEL/METATARSAL STRUCTURE HAVING TAPERED STABILIZING BULGES

[75] Inventors: Karl M. Schmidt, Woodside; Stuart E. Jenkins, Thousand Oaks; George S. Cole, Pebble Beach, all of Calif.

[73] Assignee: Energaire Corporation, Pebble Beach, Calif.

[21] Appl. No.: 582,109

[22] Filed: Jan. 2, 1996

Related U.S. Application Data

[63] Continuation-in-part of Ser. No. 398,919, Mar. 6, 1995, Pat. No. 5,545,463, which is a continuation-in-part of Ser. No. 993,099, Dec. 18, 1992, Pat. No. 5,395,674.

[51] Int. Cl.$^6$ .............................. B32B 1/00; A43B 13/20
[52] U.S. Cl. .......................... 428/178; 428/76; 428/192; 428/212; 428/172; 36/29; 36/35 B; 36/37
[58] Field of Search .................... 428/178, 76, 172, 428/72, 212, 192, 156; 36/35 B, 29, 35 R, 44, 30 R, 37

[56] References Cited

U.S. PATENT DOCUMENTS 4,577,417  3/1986  Cole ........................................ 36/29
4,869,939  9/1989  Santo ...................................... 428/178
5,395,674  3/1995  Schmidt et al. ....................... 428/178
5,545,463  8/1996  Schmidt et al. ....................... 428/178

*Primary Examiner*—Donald Loney
*Attorney, Agent, or Firm*—Emrich & Dithmar

[57] ABSTRACT

A generally U-shaped bulge having a bight portion and elongated leg portions and defining a correspondingly-shaped cavity is molded into the heel portion and/or the metatarsal portion of the outer bottom member of a shoe, the cavities tapering in depth and width from the bight portion to the distal ends of the leg portions. The bulge is disposed and oriented so as to provide a cushioning and lifting effect, and the leg portions are spaced apart a distance substantially greater than their width and are disposed closer to the peripheral edge of the member than to the longitudinal axis thereof for providing improved lateral stability. The bulges may communicate with associated cavities by narrow passageways or may function independently of other bulge structures formed in the member.

25 Claims, 12 Drawing Sheets

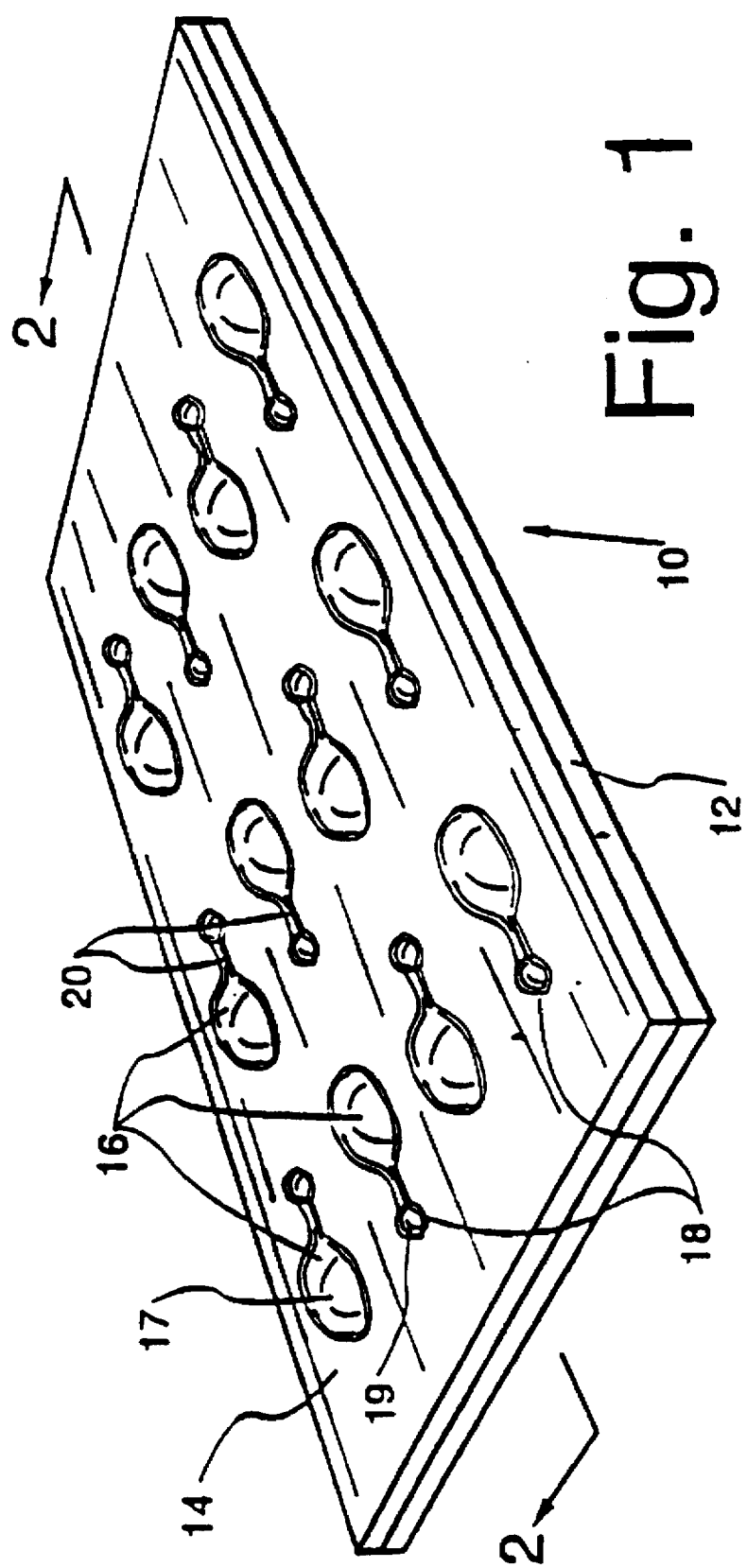

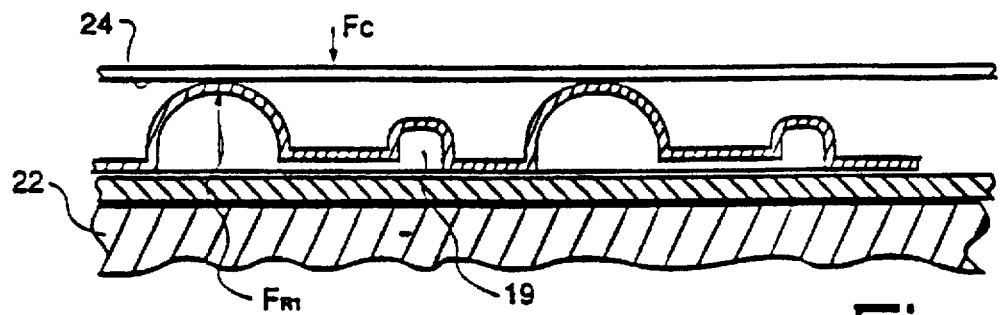
Fig. 2a
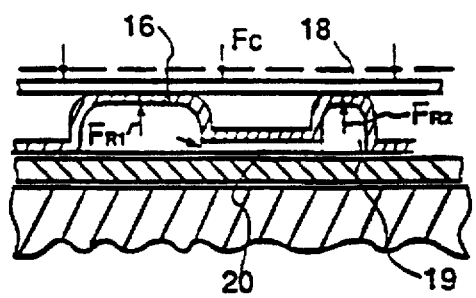
Fig. 2b
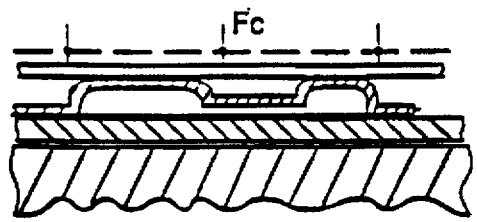
Fig. 2c
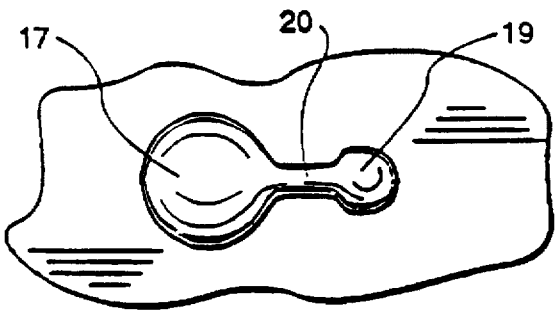
PLAN VIEW Fig. 2d

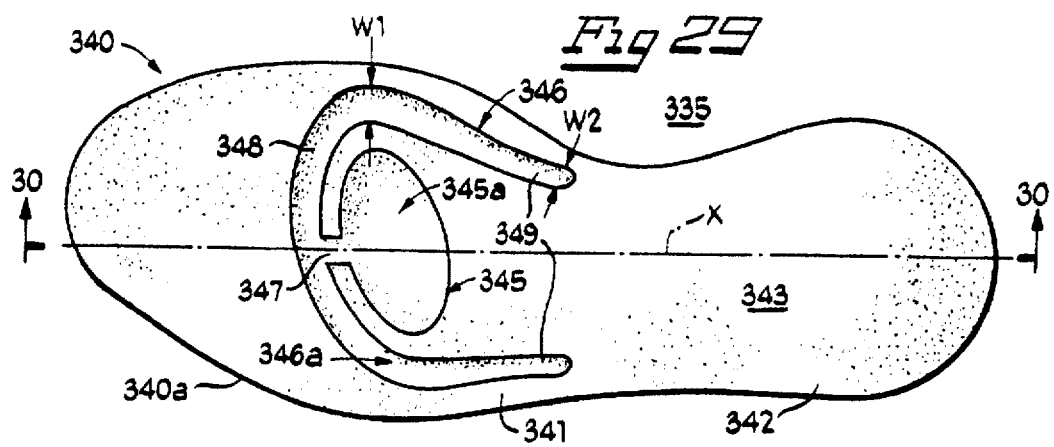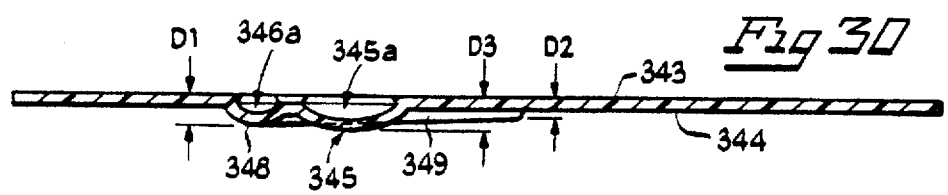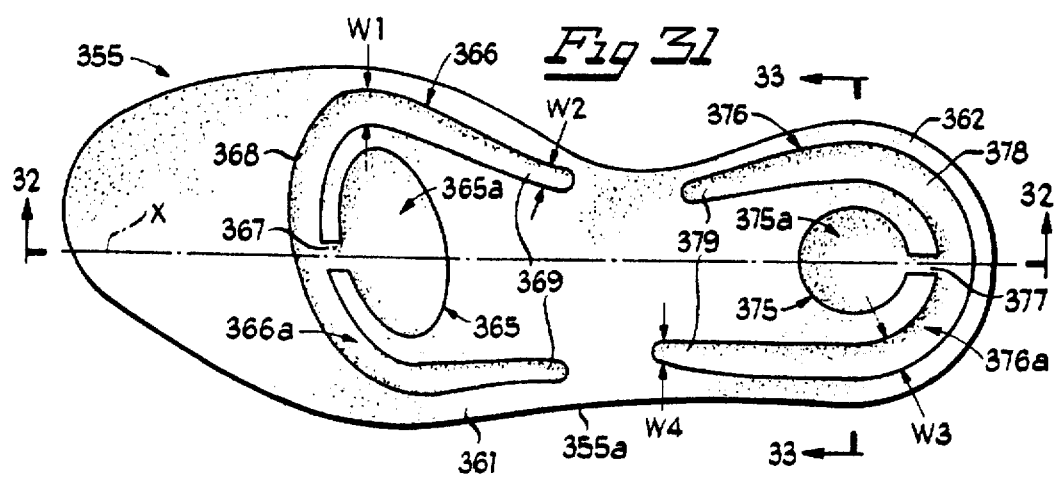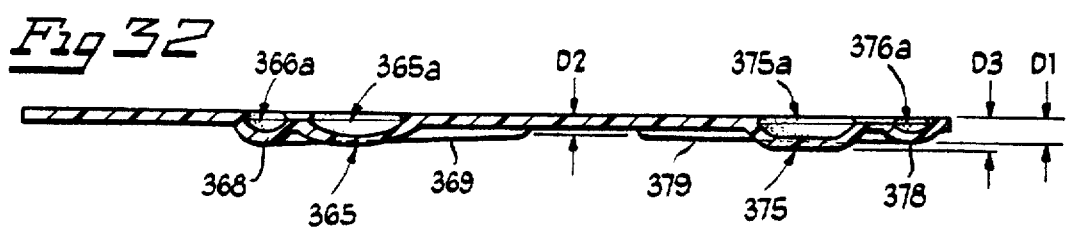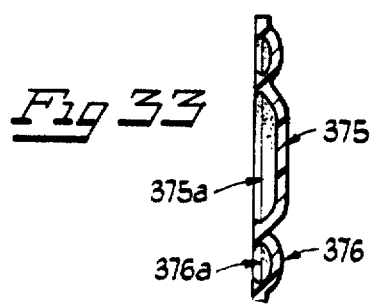

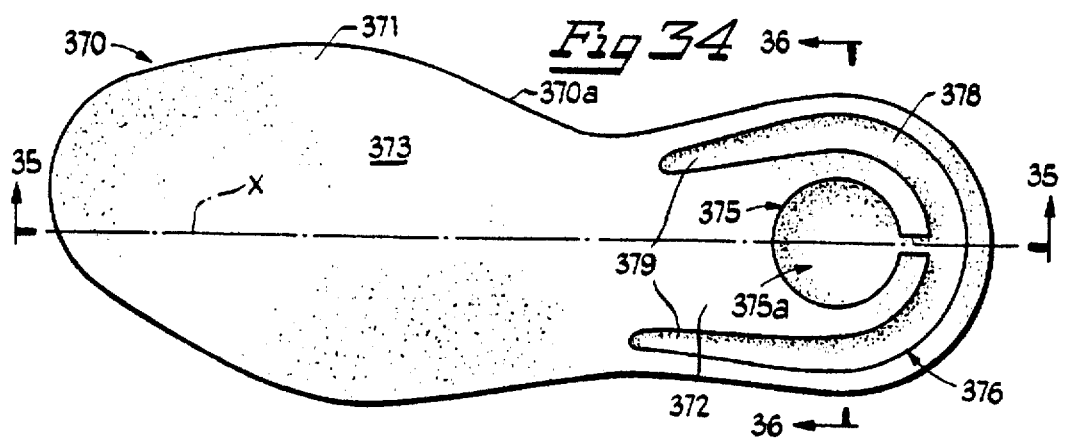
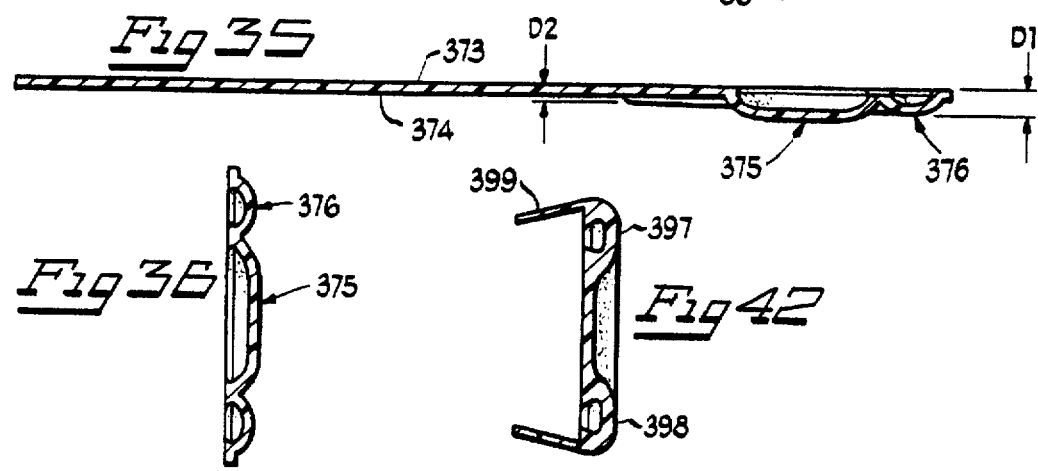
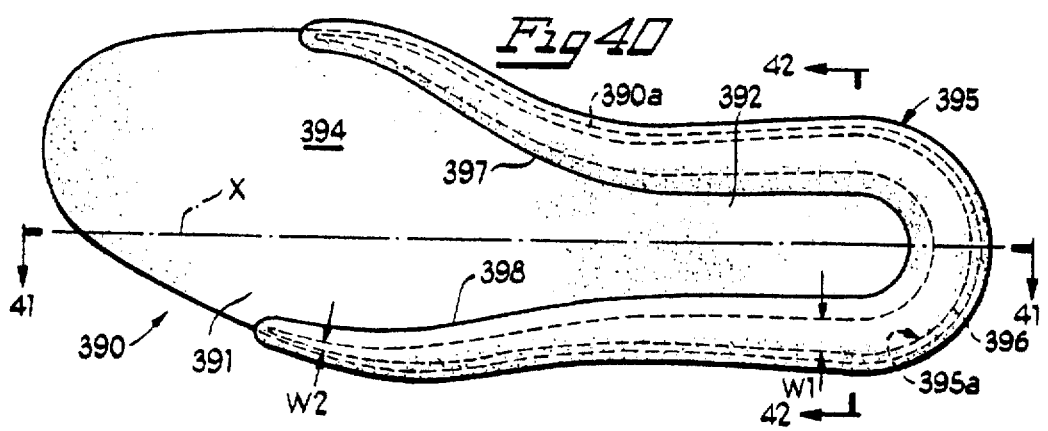
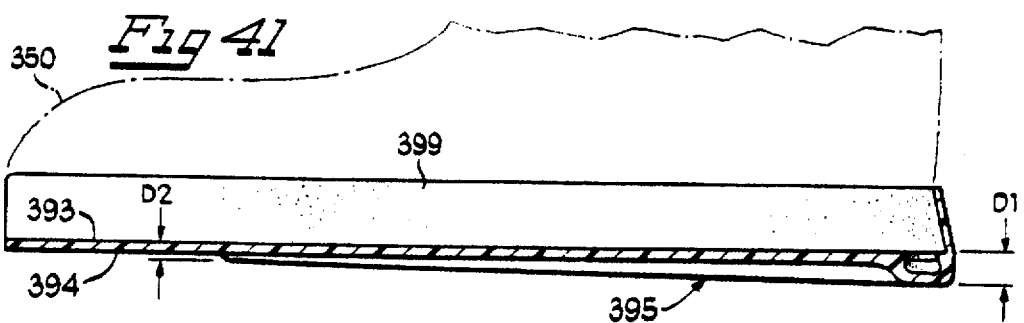

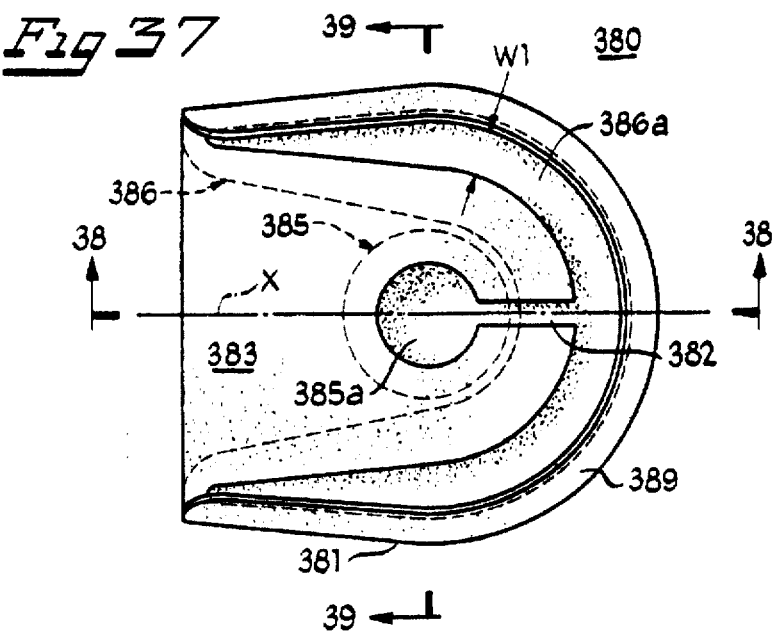
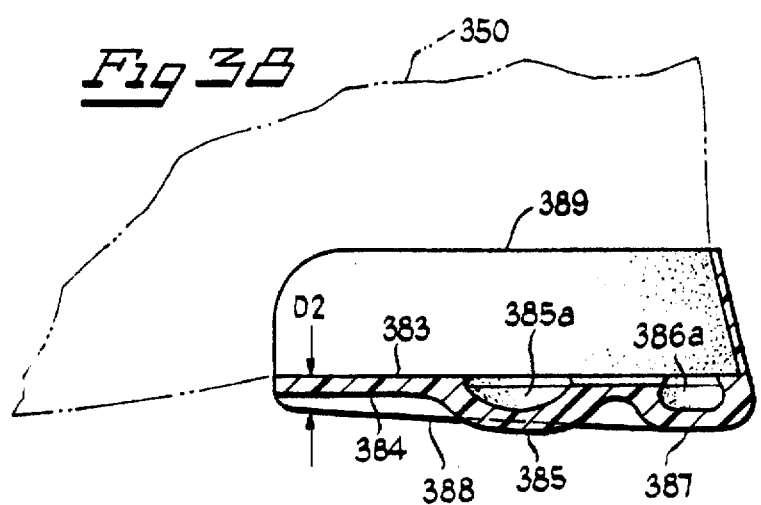
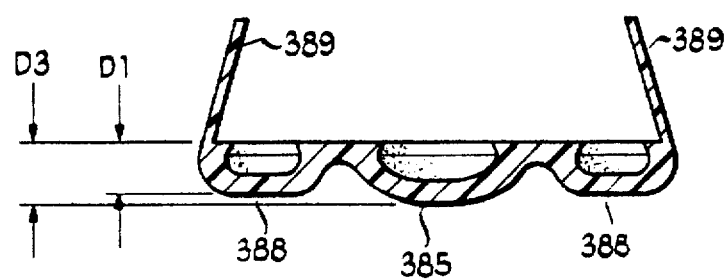

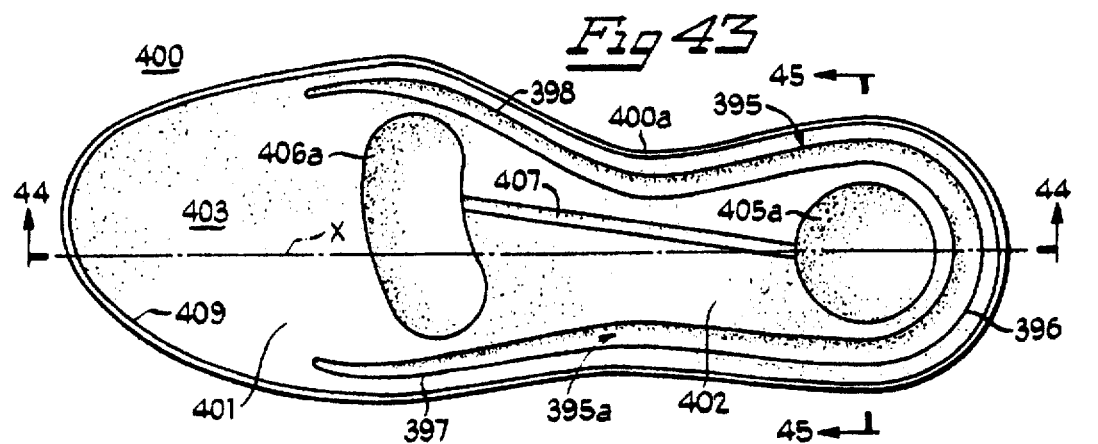
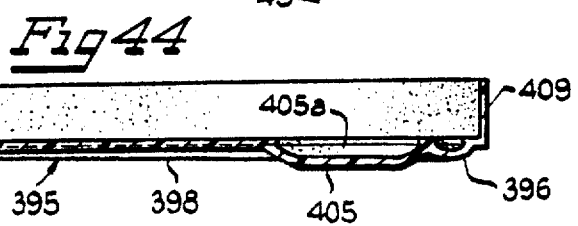
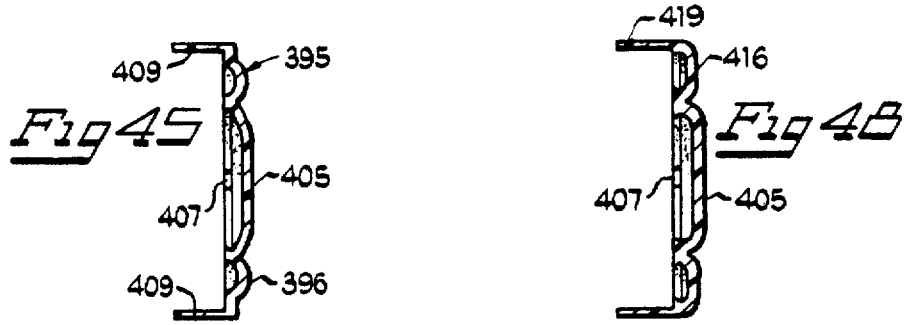
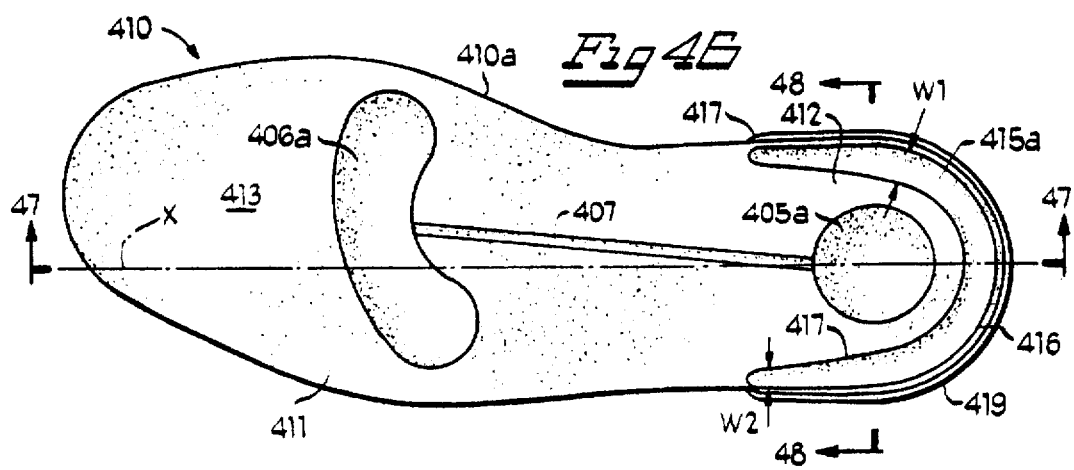
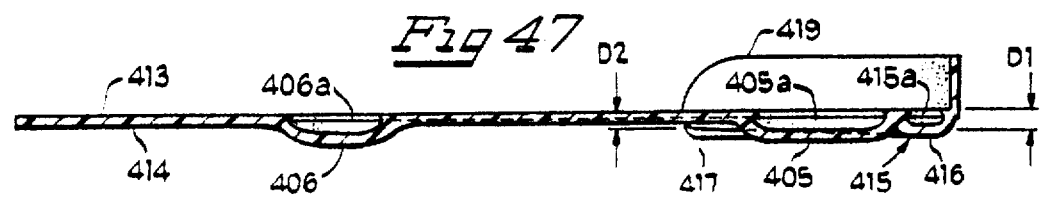

5,679,439

1

HEEL/METATARSAL STRUCTURE HAVING TAPERED STABILIZING BULGES

CROSS-REFERENCE TO RELATED APPLICATION

This is a continuation-in-part of U.S. application Ser. No. 08/398,919, filed Mar. 6, 1995 now U.S. Pat. No. 5,545,463, which is, in turn, a continuation-in-part of U.S. application Ser. No. 07/993,099, filed Dec. 18, 1992 now U.S. Pat. No. 5,395,674, issued Mar. 7, 1995.

BACKGROUND OF THE INVENTION

U.S. Pat. No. 4,577,417, assigned to the same assignee as the present application, discloses a sole-and-heel structure having a U-shaped, premolded bulge under the heel region and a premolded bulge under the metatarsal region, which bulges may or may not be interconnected by a passageway between the two bulges. If the bulges are interconnected, air in the cavities defined by the two bulges moves back and forth in the passageway. The U-shaped bulge has a bight portion and forwardly extending leg portions. While the leg portions afford some lateral stability, they are quite wide, each leg portion having a width greater than the distance therebetween. Also, each leg portion is spaced closer to the center line of the sole-and-heel structure than to the outer edge thereof, limiting the lateral stability afforded thereby. Furthermore, because of the widths of the leg portions, they are relatively flexible and compressible, which also limits the lateral stability. While the leg portions of the U-shaped bulge are somewhat tapered in depth, their relatively large, untapered width results in a "fat" shape which minimizes any movement of air within the U-shaped cavity.

SUMMARY OF THE INVENTION

It is a general object of the invention to provide an improved sole-and-heel structure which avoids the disadvantages of prior structures while affording additional structural and operating advantages.

An important feature of the invention is the provision of a shoe sole and/or heel structure which includes an elongated bulge molded into a heel portion and/or a metatarsal portion of a molded, one-piece, resilient outer member, the bulge being configured and disposed so as to provided improved lateral stability.

In connection with the foregoing feature, another feature of the invention is the provision of a shoe sole and/or heel structure of the type set forth, wherein the bulge has leg portions which are relatively thin, narrow and closely adjacent to the outer edge of the structure, so as to be relatively incompressible.

In connection with the foregoing features, a still further feature of the invention is the provision of a shoe sole and/or heel structure of the type set forth, wherein the bulge is generally U-shaped and the leg portions are tapered, so that air compressed into the leg portions will be forced back into the bight portion upon lifting of the bulge from the ground.

Another feature of the invention is the provision of a shoe sole and/or heel structure of the type set forth wherein the U-shaped bulge is connected to another bulge by a restricted passageway.

These and other features of the invention are attained by providing shoe sole and/or heel structure comprising: an outer member including a heel portion and/or a metatarsal portion and having an exterior surface and a peripheral edge and a longitudinal axis, and an elongated bulge formed in

2 one of the portions and projecting from the exterior surface and defining an elongated fluid-containing cavity, the bulge having an elongated leg portion disposed closer to the peripheral edge than to the longitudinal axis and extending along the peripheral edge from a first end to a second end, the cavity having a cross-sectional area which tapers from a maximum value at the first end of the leg portion to a minimum value at the second end of the leg portion.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWING

For the purpose of facilitating an understanding of the invention, there is illustrated in the accompanying drawings preferred embodiments thereof, from an inspection of which, when considered in connection with the following description, the invention, its construction and operation, and many of its advantages should be readily understood and appreciated.

FIG. 1 is a perspective view of an air sheet having units of bulges interconnected by passageways;

FIGS. 2a, 2b, and 2c are cross-sections taken along the line 2—2 of FIG. 1 at different stages of compression;

FIG. 2d is a plan view of one unit of FIG. 1;

FIG. 29 is a top plan view of a heel/sole structure incorporating another embodiment of the present invention;

FIG. 30 is a sectional view along the line 30—30 of FIG. 29;

FIG. 31 is a top plan view of a heel/sole structure incorporating another embodiment of the present invention;

FIG. 32 is a sectional view along the line 32—32 of FIG. 31;

FIG. 33 is a sectional view along the line 33—33 of FIG. 31;

FIG. 34 is a top plan view of a heel/sole structure incorporating another embodiment of the present invention;

FIG. 35 is a sectional view along the line 35—35 in FIG. 34, with an upper portion of an associated shoe shown in phantom;

FIG. 36 is a sectional view taken along the line 36—36 in FIG. 34;

FIG. 37 is a top plan view of a heel structure incorporating another embodiment of the invention;

3

Figure 3:
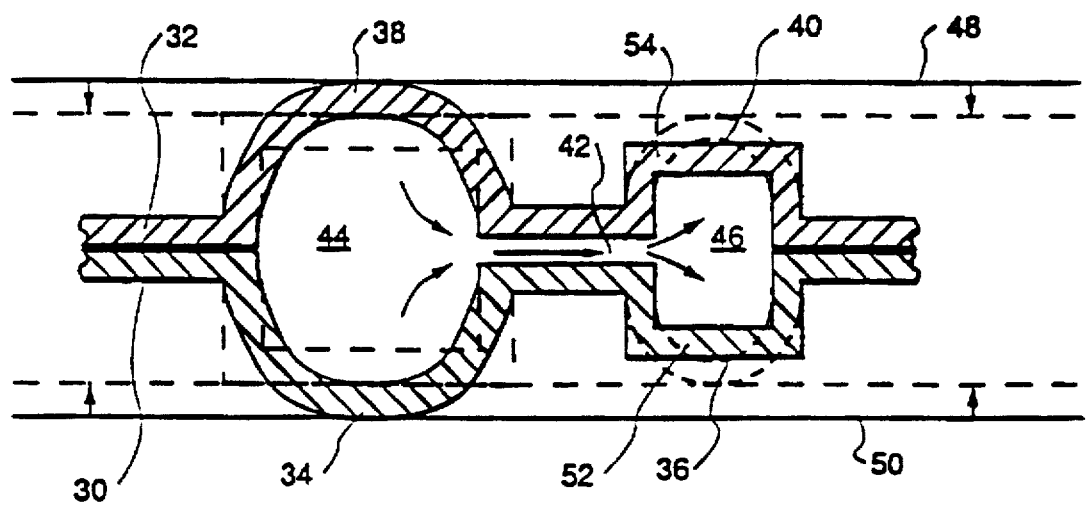
FIG. 3 is a cross-sectional view of an alternative configuration.

FIG. 38 is a sectional view taken along the line 38—38 in FIG. 37 with an upper portion of an associated shoe shown in phantom;

FIG. 39 is a sectional view taken along the line 39—39 in FIG. 37;

FIG. 40 is a bottom plan view of a heel/sole structure incorporating another embodiment of the invention;

FIG. 41 is a sectional view along the line 41—41 in FIG. 40 with an upper portion of an associated shoe illustrated in phantom;

FIG. 42 is a sectional view along the line 42—42 in FIG. 40;

FIG. 43 is a top plan view of a heel/sole structure incorporating another embodiment of the invention;

FIG. 44 is a sectional view along the line 44—44 in FIG. 43, with an upper portion of an associated shoe shown in phantom;

FIG. 45 is a sectional view along the line 45—45 in FIG. 43;

FIG. 46 is a top plan view of a heel/sole structure incorporating another embodiment of the invention;

FIG. 47 is a sectional view along the line 47—47 in FIG. 46, with an upper portion of an associated shoe shown in phantom; and FIG. 48 is a sectional view along the line 48—48 in FIG. 46.

DESCRIPTION OF THE PREFERRED EMBODIMENTS

Referring now to FIG. 1 of the drawings, a sheet of shock absorbing material 10 includes a flat or planar configured base sheet 12 overlaid by a top sheet 14 of resilient or elastic material deformed upwardly at regular intervals to define upwardly extending, but downwardly open, relatively large bubbles or bulges 16 forming cavities 17, and adjacent smaller bubbles or bulges 18 forming cavities 19, the two being joined together by a communicating passageway 20. The upper sheet 14 is glued or otherwise bonded to the lower base sheet 12 so as to form a laminated pad and close the relatively large cavities 17 in bulges 16 and the relatively small cavities 19 in smaller bulges 18. The cavities 17 and 19 of each large/small pair are intercommunicated by a passageway 20 which is closed on the lower side by the base sheet 12. The cavity pairs are organized and oriented to achieve high density over the upper surface area of the pad.

Although the cavity sizes are depicted in FIG. 1 as large compared to the thickness of the sheet, it is to be understood that, depending on the intended application, the "large" cavities can range from small fractions of an inch in diameter to several inches in diameter. The dimensions of the smaller cavities would be scaled proportionally smaller. Similarly, the thickness of the sheet or sheets 12, 14 can range from extremely thin membrane thicknesses to large thicknesses of several inches or more.

Referring now to FIG. 2a, which is a partial cross-sectional view taken along the line 2—2 of FIG. 1, it will be observed that if the pad is laid upon a planar supporting surface 22 and a compressive force $F_c$ is applied to the top of the pad by means a planar member 24, the larger bulges will be engaged and will initially resiliently resist the compression. However, as they are compressed, as depicted in FIG. 2b, the air or other fluid contained within the bulges 16 will be forced through passageways 20 into the smaller cavities 19, causing the bulges 18 to expand and rise up to be engaged by the surface 24. This is to say that as bulges

4

16 are collapsed they exert an upwardly directed resisting force $F_{R1}$ upon the member 24. At this point, further downward movement of the member 24 will cause both bulges 16 and 18 to be resiliently collapsed, as depicted in FIG. 2c, with a second resisting force $F_{R2}$ being additionally exerted by the bulge 18 of each pair. It will thus be noted that the resilient resistance to compression is nonlinear and, in fact, tends to operate in step-like fashion as the sheet is compressed. That is, during the initial stage of compression the resisting force $F_{R1}$ is generated as the fluid within cavity 17 is compressed and as the smaller cavity 19 is expanded upwardly; during the second stage of compression, the two bulges 16 and 18 are simultaneously compressed and jointly exert a total resisting force $F_{RT}=F_{R1}=F_{R2}$, as the pad is driven to maximum compression, as illustrated in FIG. 2c.

A plan view of a unit of the pad of FIG. 1, comprising a large bulge 16 and a small bulge 18, is illustrated in FIG. 2d.

FIG. 3 is a cross-sectional view taken through a unit of an alternative pad embodiment, wherein the bottom sheet of material 30, instead of being planar, is deformed to include downwardly extending bulges 34 and 36 in mirror-image correspondence to bulges 38 and 40 of upper sheet 32, such that a greater volume of fluid may be contained within the respective cavities 44 and 46. At least one of the sheets is provided with a passageway 42 for communicatively coupling the cavities 44 and 46.

In this configuration, as the larger bulges are collapsed by engagement between two members 48 and 50, the smaller bulges expand, both upwardly and downwardly, to engage the compressing surfaces and provide increased resilient resistance to compression. Whereas, the larger bulges 34 and 38 in the upper and lower sheets are generally hemispherical in configuration, the smaller bulges 36 and 40 are configured more pill-box in shape, so to provide surfaces 52 and 54 which will readily expand upwardly and downwardly when subjected to increased internal pressure, as would result from compression of the larger bulges 34, 38.

The smaller cavity 46 need not extend outwardly on both sides of the planes of the sheets 30 and 32. In some application it may be desirable that the small cavities extend in only one direction.

Figure 4:
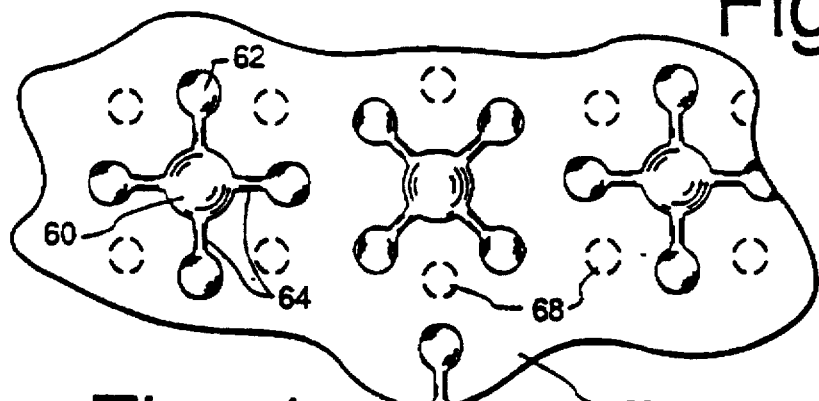
FIG. 4 is a plan view of an alternative configuration.

In FIG. 4, a plurality of larger central bulges 60 are each surrounded by an array of smaller satellite bulges 62 joined thereto by passageways 64. The large bulge/small bulge combinations, typically formed along the lines described above, are alternately rotated so as to provide a uniform distribution and high density of cavities across the surface of the material 66 forming the pad. In addition, for some applications it may be appropriate to add holes through the sheet material, as shown by the dotted circles 68, to allow air or liquid to pass through the pad from one side to the other.

Figure 5:
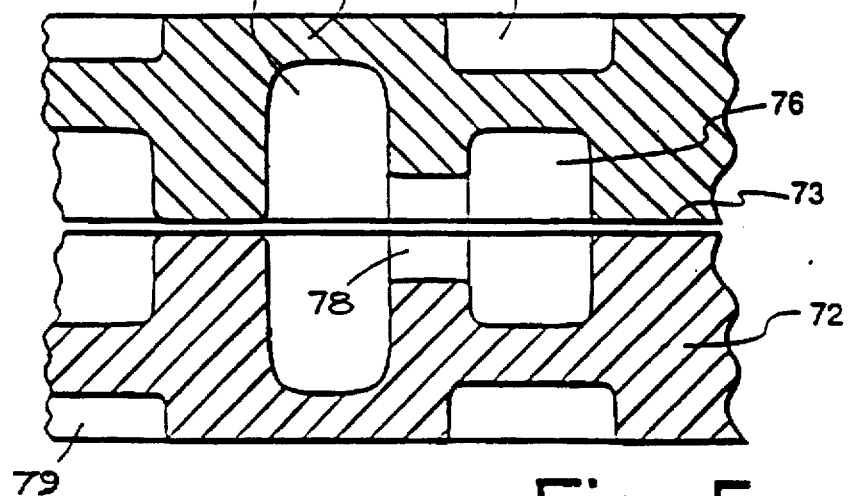
FIGS. 5 and 6 are cross-sectional views of alternative configurations.

In FIG. 5, two sheets 70 and 72 of molded compressible material are joined at 73 to form a pad having substantially flat outer surfaces. Large and small cavities 74 and 76 and communicating passageways 78 are molded into the facing surfaces of the sheets 70 and 72, and small open cavities 77 and 79 are formed in the outer surfaces above the smaller cavities 76 in order to allow such cavities to herniate outwardly to meet and engage the compressing surfaces.

Figure 6:
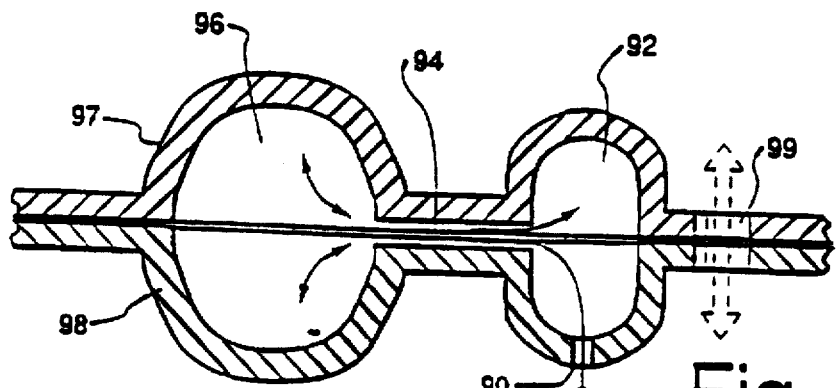

FIG. 6 depicts a cross-section similar to that of FIG. 3 and includes the addition of an opening 90 in one of the walls forming the small cavity 92 which, via passageway 94, is in communication with a larger cavity 96. In operation, compression of cavity 96 would force air out of passageway 94 and, assuming the materials forming the sheets 97 and 98 are sufficiently resilient, removal of the compressive force would allow the materials to return to their undeformed state and cause the expelled air to return through the opening 90. By judicious selection of the size of the opening or openings 90, a throttling function can be effected to modify the damping rate of the shock-absorbing action. Holes 99 may be included to allow air or liquid to pass through the pad formed by the sheets 97 and 98.

Figure 7:
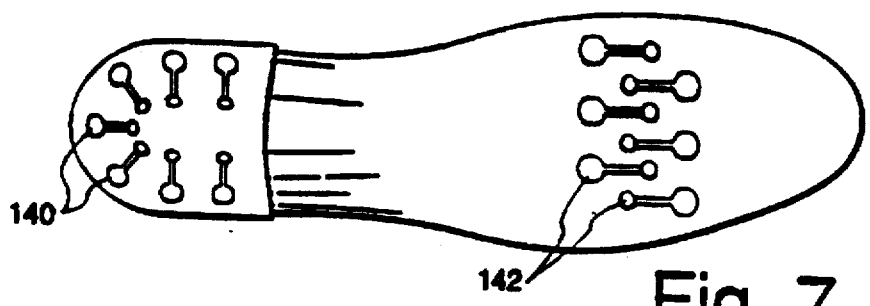
FIGS. 7, 8 and 9 illustrate the air sheet on shoe soles.
Figure 8:
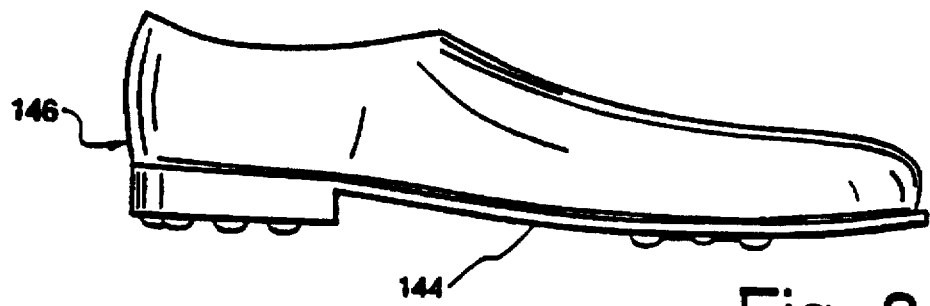

FIGS. 7 and 8 depict embodiments particularly suited for footwear applications. As illustrated, a plurality of the "pumping units" 140 and 142 of the type shown in FIGS. 1–6 are strategically positioned in the heel and metatarsal portions of the outer sole 144 of a shoe 146 to provide superior shock absorption. The large and small bulges act as studs adding to shoe traction while, at the same time, cushioning the forces applied to the shoe wearer's heel and the balls of his or her feet.

Figure 9:
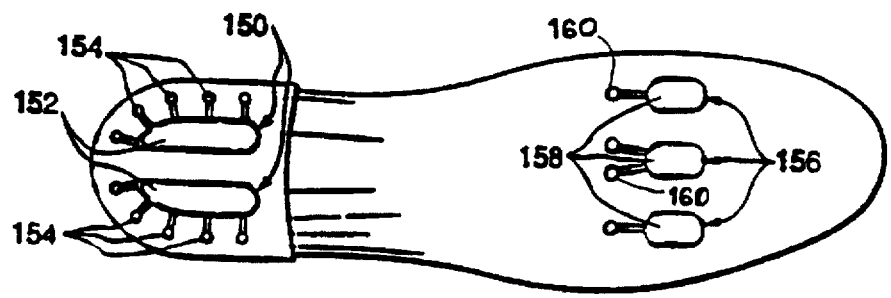

In FIG. 9, a plurality of pumping units is provided in the heel and metatarsal portions of a shoe. In the heel, two multiple-bulge units 150 are provided. Two larger bulges 152 are disposed on each side of the longitudinal centerline of the shoe and communicate with smaller bulges 154 which are arranged around the outer perimeter of the heel. These units will, in addition to their shock-absorbing function, serve to provide lateral stability to the heel. Each of three metatarsal units 156 has a large bulge 158 positioned directly under the ball of the foot. Smaller bulges 160 are positioned rearwardly of the bulges 158 and communicate therewith so as to provide a forward lift as they are inflated. Those skilled in the shoe art will readily appreciate that various combinations and arrays of the pumping units of the present invention can be used in footwear to add stability and to correct supination and pronation problems.

The multi-cavitied configurations depicted in the drawing and described hereinabove form small pumping mechanisms which actively resist the collapse or compression of the sheet or other shaped material in which they are formed. The basic principle of the miniature pumps is that air or other fluid trapped in the larger ball-shaped cavities, which in most embodiments protrude from the plane of the sheet, when compressed, will pass the compressed fluid through a narrow passageway to a smaller cavity which then expands to meet a compressing surface and add its resisting force to counter the compressing action. By way of example, should a weight be dropped upon a pad of the type depicted in FIGS. 1 and 2, there will be a decelerating effect at a first rate as the weight compresses the larger cavities, forcing fluid into the smaller cavities, which expand to meet the weight. As the weight meets the expanded smaller cavities, and tends to compress them along with the larger cavities, the weight will be caused to decelerate at a second rate, etc. Accordingly, the functionality of the present invention differs materially from prior art resilient pads, bubble packs and the like.

Figure 10:
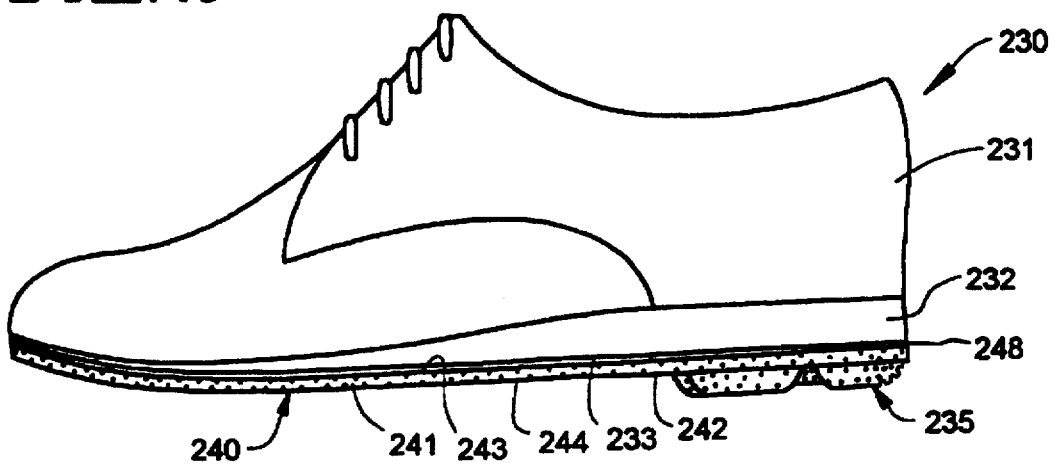
FIG. 10 is a side elevational view of a shoe embodying heel structure incorporating the features of the present invention.

Turning to FIG. 10, there is depicted a shoe 230 having a conventional upper portion or last 231 and a so-called mid-sole 232, which is generally of wedge shape, whereby the shoe 230 is referred to as being of the "wedge-type." The mid-sole 232 has a downwardly facing surface 233.

Figure 11:
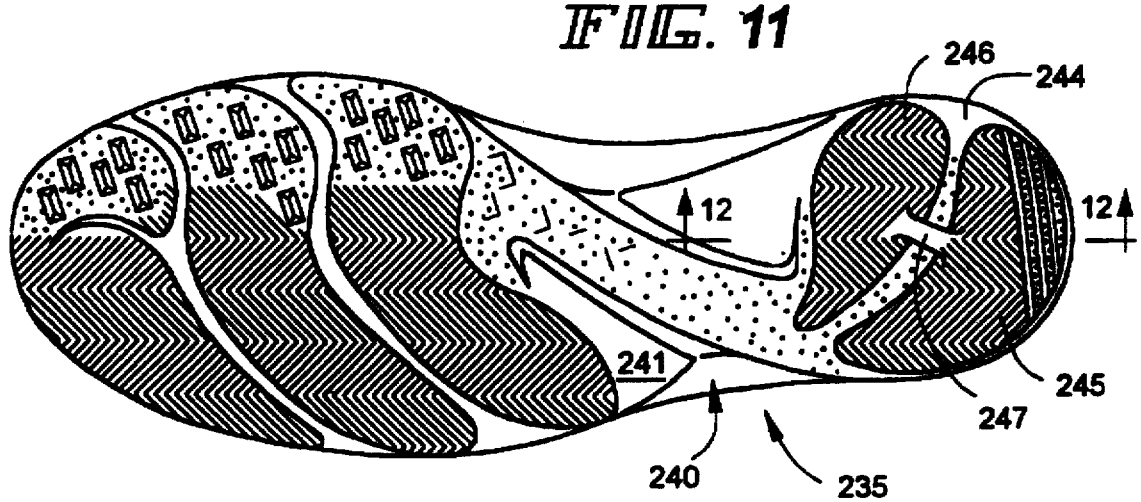
FIG. 11 is a bottom plan view of the shoe of FIG. 10 on an enlarged scale.
Figure 12:
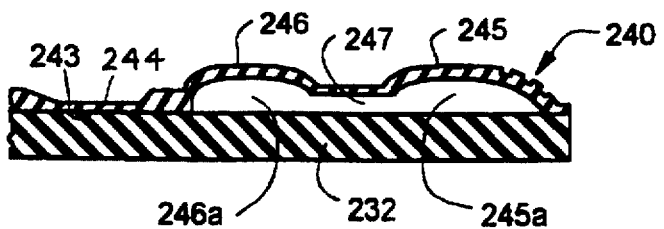
FIG. 12 is a fragmentary view in longitudinal section of the heel structure, taken along the line 12—12 of FIG. 11, on an enlarged scale.

Referring also to FIGS. 11 and 12, a sole-and-heel structure 235 is affixed to mid-sole 232. Structure 235 comprises a generally flat, thin, elongated outer member 240 of one-piece, molded construction, preferably formed of rubber. In an operative embodiment, the member 240 had a thickness of 0.125 inch. It is essential that member 240 be highly wear resistant, since it is subject to engagement with the pavement, floor or other underlying support surface (hereinafter "the ground"). A preferred composition is made by Goodyear Tire & Rubber Company under its brand name INDY 500.

Member 240 has a sole portion 241 located under the sole of a wearer's foot and a heel portion 242 located under the wearer's heel. Outer member 240 has a substantially planar interior surface 243 and an exterior surface 244 which contacts the ground. First and second bulges 245 and 246 are molded into heel portion 242 and project downwardly from exterior surface 244. Bulges 245 and 246 respectively define cavities 245a and 246a opening to interior surface 243. In a preferred embodiment, the cavity 245a is larger than cavity 246a. A restricted passageway 247 is molded into outer member 240, between cavities 245a and 246a and opening to interior surface 243. Between surface 243 of outer member 240 and surface 233 of mid-sole 232 is an adhesive 248 (FIG. 10). Outer member 240 and mid-sole 232 are thus attached, and cavities 245a and 246a are hermetically sealed, whereby air at atmospheric pressure is permanently located in the space jointly defined by cavities 245a and 246a and passageway 247.

In use, bulges 245 and 246 engage the ground as the wearer of shoe 230 is standing. Air in cavities 245a and 246a provide a cushioning effect. In walking, bulge 245 comes in contact with the ground first, causing air in cavity 245a to be compressed and forced through passageway 247 into cavity 246a. As heel portion 242 lifts off the ground, air returns to cavity 245a to give a lifting effect.

In a preferred embodiment, surface 244 has a tread such as is used in athletic shoes. Although a wedge-type shoe is depicted, a structure in which the forward part of the heel structure is substantially vertical can be formed.

In this embodiment, there are two heel bulges and a passageway between the two. The basic concept is that air is used first to cushion, then to control the motion of the foot while walking or standing. During walking, a relatively large amount of air is moved into a smaller volume through a restricted passageway 247. Passageway 247 reduces the speed at which air moves out of main cavity 245a, thus providing cushioning. The fact that air moves from a large cavity to a small cavity 246a also provides support in the area of cavity 246a.

It is important that the small cavity 246a be pressurized from a larger air cavity 245a so that when the weight is moved by virtue of the foot being lifted for stepping, air will flow back into the larger cavity 245a in order to be ready for the next foot strike.

Large cavity 245a is for cushioning. The smaller front cavity 246a is on the medial side of the foot and will help reduce pronation, that is, the rolling of the foot to the inside.

In walking, bulge 245 strikes first, giving a cushion to the strike. Then, air is forced through passageway 247 to inner bulge 246, which prevents the foot from turning inward. The air further cushions the heel and returns to outer bulge 245 as the weight is shifted forward and eventually lifted, preparing the outer bulge 245 for the next strike.

Instead of the heel portion being part of a heel-and-sole structure, a separate heel portion can be provided.

Because the cavity 245a is larger than cavity 246a, cavity 246a is over-inflated, which then forces the air back to the cavity 245a at a faster rate. This gives the heel a slight lift during walking. Air will be forced to bulge 245 and provide a slight lift to the heel as the weight rotates forward. Cavities 245a and 246a are basically fixed in size; they do not expand any significant amount.

Figure 13:
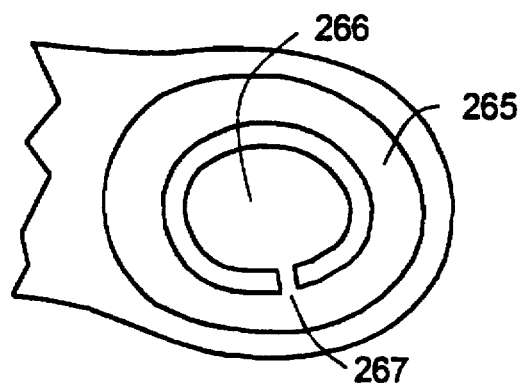
FIGS. 13–28 depict fragmentary heel portions of a shoe incorporating various embodiments of the present invention.
Figure 14:
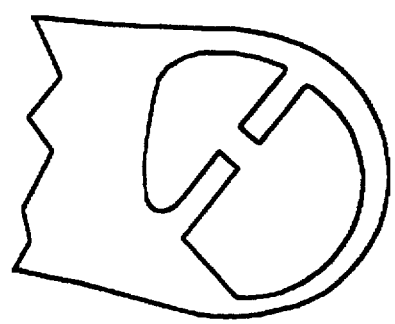
Figure 15:
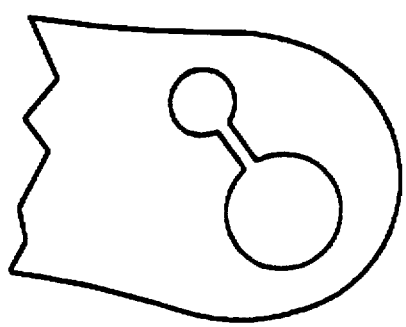
Figure 16:
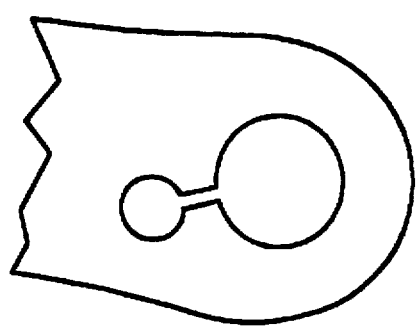

In the embodiment of FIG. 13, heel bulge 266 has a generally rounded shape and is surrounded by a toroidshaped bulge 265 with a passageway 267 between the bulges. In this embodiment, as in the rest of the embodiments, each bulge defines a similarly shaped cavity. Air moves back and forth between the two cavities by way of passageway 267. The embodiments in each of FIGS. 14 to 16 have two bulges in the heel portion joined by a passageway.

Figure 17:
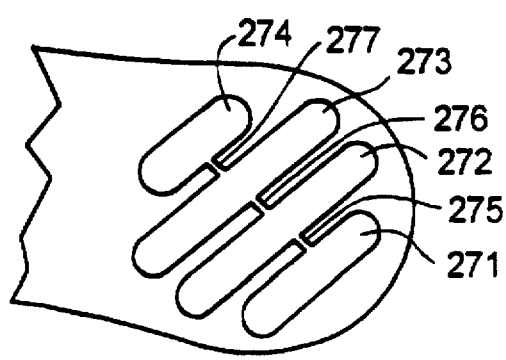
Figure 18:
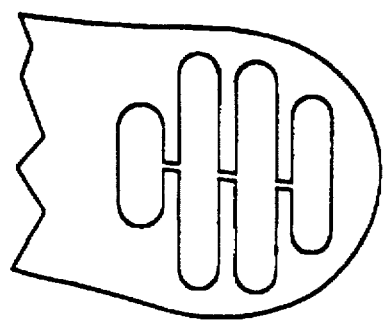

In the embodiment of FIG. 17 there are four elongated bulges 271 to 274 joined by three passageways 275 to 277, as shown. Air moves back and forth among the cavities defined by these bulges by way of such passageways. FIG. 18 depicts a similar construction, but of different orientation.

Figure 19:
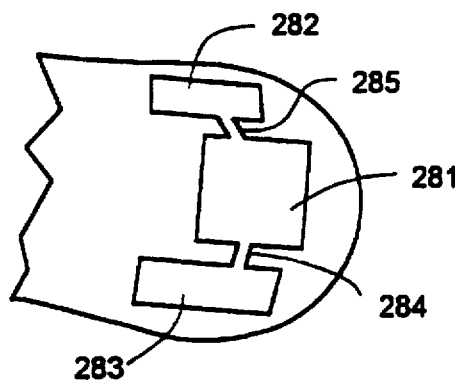

In the embodiment of FIG. 19, a larger bulge 281 is located between two smaller bulges 282 and 283. Passageway 284 connects the cavities defined by bulges 281 and 283. Passageway 285 connects the cavities defined by bulges 281 and 282. Preferably the volume of air in the cavity defined by bulge 281 is approximately the volume of combined air in the cavities defined by bulges 282 and 283.

Figure 20:
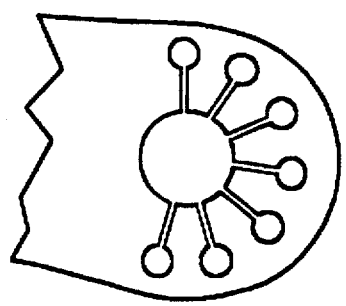
Figure 21:
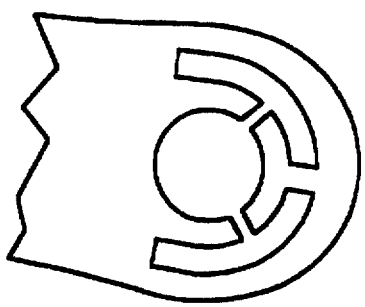
Figure 22:
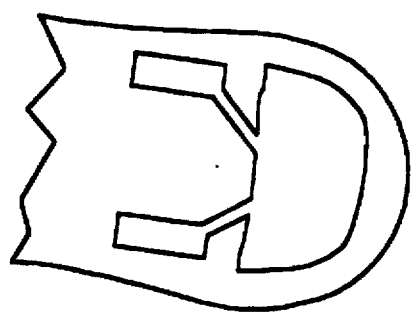
Figure 23:
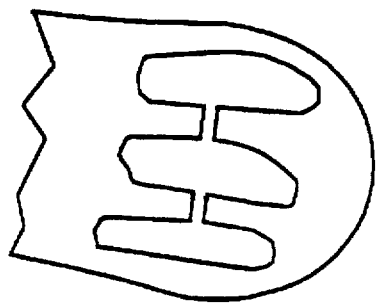
Figure 24:
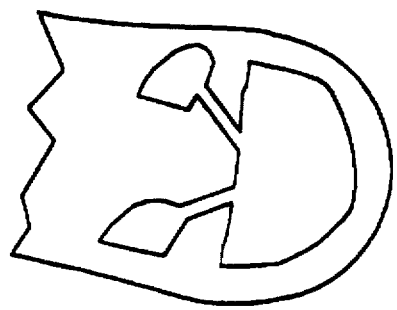

In the embodiment of FIG. 20, seven small cavities extend from one large central cavity byway of seven passageways. The embodiments of FIGS. 21, 22 and 24 are similar to the embodiment of FIG. 19, in that there is one large cavity and two smaller cavities, all under the heel, connected by way of a pair of passageways. In the embodiment of FIG. 23, there are three bulges of generally the same size.

Figure 25:
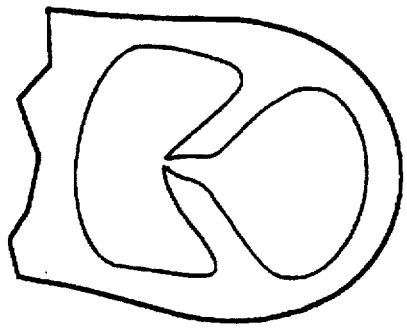
Figure 26:
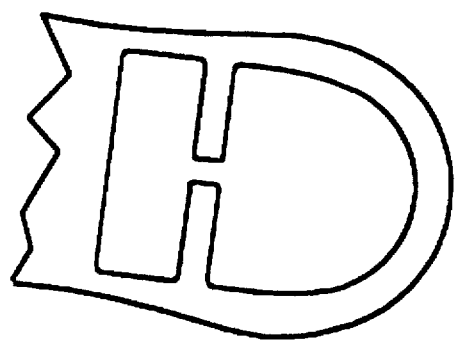
Figure 27:
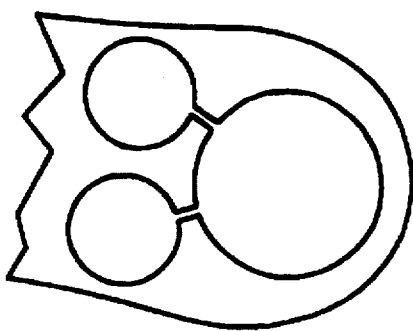
Figure 28:
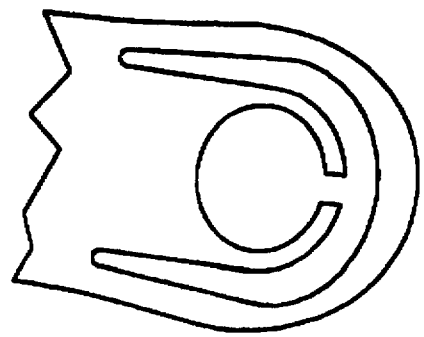

In the embodiments of FIGS. 25, 26 and 28 a pair of cavities has a pair of bulges joined by a passageway. In the embodiment of FIG. 27, two smaller bulges are connected by passageways to a larger, more rearwardly located bulge.

Referring to FIGS. 29 and 30, the sole-and-heel structure 335 depicted therein includes a generally flat, thin, elongated outer member 340 of one-piece, molded construction, preferably of rubber, like member 240.

Member 340 is bounded by a peripheral edge 340a and has a metatarsal portion 341 located under the metatarsal region of the wearer's foot and a heel portion 342 located under the person's heel. Outer member 340 has a substantially planar interior surface 343 and an exterior surface 344 which contacts the ground. First and second bulges 345 and 346 are molded into metatarsal portion 341 and project downwardly from exterior surface 344. Bulges 345 and 346 respectively define cavities 345a and 346a opening to interior surface 343. A restricted passageway 347 is molded into outer member 340, between cavities 345a and 346a and opening to interior surface 343. A member (not shown) like member 232 is attached to surface 343 by adhesive, so that cavities 345a and 346a are hermetically sealed, whereby air at atmospheric pressure is permanently located in the space jointly defined by cavities 345a and 346a and passageway 347.

It is a significant aspect of the invention that the bulge 346 is generally U-shaped, having a curved bight portion 348 and two elongated leg portions 349 which extend rearwardly from the bight portion 348 straddling the bulge 345. Significantly, the bulge 346 is tapered in depth (vertical distance from the interior surface 343) from a maximum depth D1 at the bight portion 348 to a minimum depth D2 at the distal ends of the leg portions 349. It will be appreciated that the cavity 346a defined by the bulge 346 is correspondingly tapered in depth. Also, the portion of the cavity 346a defined by each of the leg portions 349 is tapered in width (distance across the cavity at the interior surface 343) from a maximum value W1 at a bight end of the leg portion to a minimum value W2 at the distal end of the leg portion. The bulge 345 has a depth D3 greater than the maximum depth D1 of the bulge 346. The leg portions 349 are spaced apart a distance substantially greater than the maximum width W1 thereof, and are, respectively, disposed closer to the peripheral edge 340a than they are to the longitudinal axis X of the outer member 340.

In use, when the wearer is standing, the bulge 345 will be compressed slightly, forcing air into the bulge 346, so that both the bulges 345 and 346 engage the ground and provide a cushioning effect. When the wearer is walking or running, the bulge 345 engages the ground first causing air in the cavity 345a to be compressed and forced through the passageway 347 into the cavity 346a. More specifically, air is forced initially into the bight portion 348 of the bulge 346 and thence into the leg portions 349 thereof. Because of their narrow configuration, the leg portions 349 of the bulge 346 are relatively stiff and incompressible. Thus, they tend to serve as rigidifying members which, because of their location closely adjacent to and running alongside the peripheral edge 340a at the sides of the outer member 340, provide significantly improved lateral stability. Because of the tapered configuration of the leg portions 349, the cross-sectional area of the cavity 346a reduces toward the distal ends of the leg portions 349, causing the air forced thereinto to become significantly compressed. Thus, as the metatarsal portion 341 lifts off the ground, this increased pressure forces the air to return to the cavity 345a to give a lifting effect.

The design of FIGS. 29, 30 is used mainly in sports or for people with metatarsal problems. The bulges are placed to absorb the shock of impact on the metatarsal bulge from jumping or playing tennis, for example, wherein the person is more on his or her toes. The center bulge 345 absorbs the initial shock, forcing the air through passageway 347 into the outer bulge 346. The air bulge 346 is compressed and acts to stabilize the foot while it is on its metatarsal and also acts as a cushion. Then, when the foot is lifted, the compressed air in the leg portions 349 is forced back into the bight portion 346 and then into the center larger bulge 345.

In a preferred embodiment, surface 344 has a tread such as is used in athletic shoes.

The above-described embodiment is particularly desirable in a woman's high-heel shoe, in which a pad could be used on the heel portion and/or a pad could be used on the metatarsal portion.

Yet another embodiment is depicted in FIGS. 31-33. This embodiment includes an outer member 355 having a peripheral edge 355a and metatarsal and heel portions 361 and 362. Member 355 has bulges 365, 366 and associated cavities 365a, 366a under a metatarsal portion 361. It also has a pair of bulges 375, 376 and associated cavities 375a, 376a under heel portion 362. The cavities 375a, 376a in the heel portion are joined by a passageway 377 and the cavities 365a, 366a in the metatarsal portion are joined by a passageway 367, but there is no passageway between the cavities of the metatarsal portion and the heel portion.

The bulges 365 and 366 and their associated cavities 365a and 366a are configured and positioned substantially the same as the bulges 345 and 346 and their associated cavities 345a and 346a, described above in connection with FIGS. 29 and 30, and function in the same way.

Similarly, the bulge 376 is generally U-shaped, having a bight portion 378 and elongated leg portions 379 which project forwardly from the bight portion 378. The bulge 376 tapers from a maximum depth D1 at the bight portions 378 to a minimum depth D2 at the distal ends of the leg portions 379, with the cavity 376a being correspondingly tapered in depth. The bulge 375 has a depth D3 greater than the maximum depth D1 of the bulge 376. The portion of the cavity 376a defined by each of the leg portions 379 tapers in width from a maximum width D3 at the bight end thereof to a minimum width W4 at the distal end thereof. The leg portions 279 are spaced apart a distance substantially greater than the maximum W3 thereof, and they extend along the peripheral edge 355a, being substantially closer thereto than they are to the longitudinal axis X of the outer member 355.

In use, the function of the bulges 375 and 376 is similar to that of the bulges 365 and 366. Thus, when the wearer is moving with a gait in which the heel strikes the ground first, the bulge 375 first engages the ground absorbing the initial shock and causing the air in the cavity 375a to be compressed and moved through the passageway 377 into the bulge 376. More specifically, the air is forced into and compressed in the tapered leg portions 379 of the bulge 376 which, because of their thin, narrow configuration are relatively stiff or incompressible. This stiffness, combined with their location closely adjacent to the peripheral edge 355a, affords significantly improved lateral stability. As the heel portion 362 comes off the ground, the elevated pressure in the leg portions 379 forces the air back into the cavity 375a, providing a lifting effect.

It will be appreciated that a sealing member (not shown) like the member 232 may be attached to the interior surface of the outer member 355, hermetically sealing air at atmospheric pressure in the cavities 365a, 366a, 375a and 376a and the passageways 367 and 377.

Referring now to FIGS. 34–36, there is illustrated a sole-and-heel structure comprising an outer member 370 which is substantially the same as the outer member 355, described above in connection with FIGS. 31–33, except that it does not include the metatarsal bulges 365 and 366. Accordingly, the different parts of the outer member 370 are designated with the same reference numerals used for corresponding parts of the outer member 355. The outer member 370 has a peripheral edge 370a, metatarsal and heel portions 371 and 372, respectively, and interior and exterior surfaces 374 and 375, respectively. The outer member 370 includes the bulges 375 and 376, which are identical to those described above in connection with FIGS. 31–33 and function in exactly the same way. Again, it will be understood that a suitable sealing member could be applied to the interior surface 373 to hermetically seal air at atmospheric pressure in the cavities 375a and 376a and the passageway 377.

Referring now to FIGS. 37–39, there is illustrated an outer heel member 380 of one-piece molded construction. The member 380 is bounded by a peripheral 381 and has a substantially planar interior surface 383 and an exterior surface 384. First and second bulges 385 and 386, respectively defining cavities 385a and 386a, are molded in the heel member 380 and project downwardly in use from the exterior surface 384. A passageway 382 molded in the member 380 interconnects the cavities 385a and 386a. The bulge 385 is circular in shape, while the bulge 386 is generally U-shaped, having a curved bight portion 387 and two elongated leg portions 388 projecting forwardly in use from the bight portion 387 and straddling the bulge 385. Integral with the outer heel member 380 and projecting upwardly therefrom along the side and rear portions of the peripheral edge 381 is an attachment flange 389, which preferably slopes upwardly and inwardly over the interior surface 383, for the purpose of facilitating attachment to associated mid-sole or other upper structure 350 (FIG. 38) of an associated shoe. It will be appreciated that such mid-sole or other upper structure 350, when secured in place, will serve to hermetically seal air at atmospheric pressure in the cavities 385a and 386a and the passageway 382.

The bulge 386 is substantially the same as the bulge 376, described above in connection with FIGS. 31–33, having a depth which tapers from a maximum value D1 at the bight portion 387 to a minimum value D2 at the distal ends of the leg portions 388, with the cavity 376a being correspondingly tapered in depth. The portion of the cavity 376a defined by each of the leg portions 388 has a width which tapers from a maximum value W1 at the bight end thereof to a minimum value W2 adjacent to the distal end thereof. In use, the functioning of the bulges 385 and 386 is substantially the same as that of the bulges 375 and 376, described above in connection with FIGS. 34–36.

Referring now to FIGS. 40–42, there is illustrated a sole-and-heel structure comprising an elongated outer member 390 of one-piece, molded construction, bounded by a peripheral edge 390a. The member 390 has a metatarsal portion 391 and a heel portion 392, a substantially planar interior surface 393 and an exterior surface 394. A generally U-shaped bulge 395 is molded into the member 390, and defines a cavity 395a. The bulge 395 has an arcuate bight portion 396 disposed in the heel portion 392 and two elongated leg portions 397 and 398, which extend forwardly from the bight portion 396, respectively along the opposite side portions of the peripheral edge 390a, and into the metatarsal portion 391. An upstanding flange 399 is integral with the outer member 390 around its perimeter adjacent to the peripheral edge 390a and projects upwardly and slightly inwardly over the interior surface 393 to facilitate attachment to an associated mid-sole or other shoe structure 350. It will be appreciated that such a structure 350 will serve to hermetically seal air at atmospheric pressure in the cavity 395a.

The bulge 395 has a depth which tapers from a maximum value D1 at the bight portion 396 to a minimum value D2 at the distal ends of the leg portions 397 and 398, the cavity 395a being correspondingly tapered in depth. Also, the portion of the cavity 395a defined by each of the leg portions 397 and 398 has a width which tapers from a maximum value W1 at the bight end thereof to a minimum value W2 adjacent to the distal end thereof. The leg portions 397 and 398 are spaced apart a distance substantially greater than the maximum width W1 of the cavity portions defined thereby. Furthermore, the leg portions 397 and 398 are disposed closer to the peripheral edge 390a than they are to the longitudinal axis X of the outer member 390. Indeed, the bulge 395, along its entire length, extends laterally outwardly slightly beyond the peripheral edge 390a.

In use, when the wearer is standing, the bulge 395 engages the ground along its entire length and provides a cushioning effect. When the wearer is moving with a gait in which the heel strikes the ground first, the bight portion 396 of the bulge 395 will first strike the ground, forcing the air within forwardly along the leg portions 397 and 398. The air is compressed as it moves into the reduced cross-sectional area adjacent to the distal ends of the leg portions 397 and 398. As the wearer's foot rolls forward, the metatarsal portion 391, including the forward ends of the leg portions 397 and 398, engage the ground and this contact, along with the elevated pressure of the air in the distal ends of the leg portions 397 and 398, forces the air rearwardly back toward the bight portion 396, providing a lifting effect. Also, because of the thin, narrow configuration of the leg portions 397 and 398, they are relatively stiff and incompressible which, together with their location along the peripheral edge 390a, provides significantly improved lateral stability.

Referring now to FIGS. 43–45, there is illustrated a sole-and-heel structure including an elongated outer sole/heel member 400, bounded by a peripheral edge 400a. The outer member 400 has a metatarsal portion 401 and a heel portion 402 and a substantially planar interior surface 403 and an exterior surface 404. Molded in the outer member 400 is an elongated, generally U-shaped bulge 395, which is substantially the same as that described above in connection with FIGS. 40–42 and which, accordingly, will not be further described. The outer member 400 also has molded therein a circular bulge defining a cavity 405a in the heel portion 402 adjacent to the bight portion 396 of the bulge 395, and an oblong bulge 406 defining a cavity 406a and disposed in the metatarsal portion 401. Each of the bulges 405 and 406 projects downwardly from the exterior surface 404, each having a depth greater than the maximum depth D2 of the bulge 395. Also molded in the outer member 400 is an elongated restricted passageway 407, which provides communication between the cavities 405a and 406a. Integral with the outer member 400 along its entire perimeter and upstanding from the peripheral edge 400a is an attachment flange 409, which is similar to the attachment flange 399, described above, except that it is substantially perpendicular to the interior surface 403 along its entire length and has a height which tapers downwardly toward the forward end of the outer member 400. Otherwise the flange 409 serves the same function as the flange 399, described above in connection with FIGS. 40–42. It will be appreciated that, as described above, mid-sole or upper structure 350 to which the outer member 400 can be attached, will serve to seal air at atmospheric pressure in the cavities 395a, 405a and 406a and in the passageway 407

In use, the bulge 395 functions in exactly the same manner as described above in connection with FIGS. 40–42. The bulges 405 and 406 and the interconnecting passageway 407 function in substantially the same manner as the corresponding structure disclosed in the aforementioned U.S. Pat. No. 4,577,417, but completely independently of the bulge 395. Thus, during a walking movement, there is a pumping action of air back and forth between the cavities 405a and 406a to give alternate lifting effects and to provide thrust at the metatarsal ball area and the heel area that facilitates walking and running.

Referring now to FIGS. 46–48, there is illustrated a sole-and-heel structure including an elongated outer sole/heel member 410 of one-piece construction, bounded by a peripheral edge 410a. The outer member 410 has a metatarsal portion 411 and a heel portion 412, as well as a substantially planar interior surface 413 and an exterior surface 414. Molded in the outer member 410 are substantially the same bulges 405 and 406 and interconnecting passageway 407 shown in FIGS. 43–45 and which function in the same manner as was described above in connection with those figures. The outer member 410 differs from the outer member 400 of FIGS. 43–45 in that, instead of the bulge 395, there is provided a generally U-shaped bulge 415, defining a cavity 415a which is confined to the heel portion 412. The bulge 415 has an arcuate bight portion 416 and a pair of elongated, forwardly extending leg portions 417 which straddle the circular bulge 405. The bulge 415 has The bulge 415 has a depth which tapers from a maximum value D1 at the bight portion 416 to a minimum value D2 at the distal ends of the leg portions 417, with the cavity 415a being correspondingly tapered in depth. Also, the cavity formed by each of the leg portions 417 has a width which tapers from the maximum value W1 at the bight end thereof to a minimum value W2 adjacent to the distal end thereof.

The leg portions 417 are spaced apart a distance substantially greater than the maximum width thereof, and each of the leg portions 417 extends along the peripheral edge 410a closer thereto than to the longitudinal axis X of the outer member 410. Integral with the outer member 410 and projecting upwardly therefrom along the perimeter of the heel portion 412 is an upstanding attachment flange 419, which is similar to the flange 409 described in connection with FIGS. 43–45, except that it terminates at the distal ends of the leg portions 417. The flange 419 facilitates attachment to a heel portion of a mid-sole or other upper structure 350, which will serve to seal atmospheric air in the cavities 405a, 406a and 415a and in the passageway 407.

In operation, the bulge 415 functions in substantially the same manner as the bulge 395, described above in connection with FIGS. 37–39, independently of the other bulges in the outer member 410.

While attachment flanges have been illustrated only in connection with FIGS. 37–48, it will be appreciated that they could also be used with the outer members described above in FIGS. 29–36. Also, it will be appreciated that, in lieu of these attachment flanges, there could be provided in the embodiments of FIGS. 37–48 a suitable sealing member, such as the member 232, for sealing atmospheric air in the associated cavities and passageways of the outer members. While tilted attachment flanges have been shown in the embodiments of FIGS. 37–42, and vertical attachment flanges in the embodiments of FIGS. 43–48, it will be appreciated that either type could be used in any embodiment, depending upon the particular configuration of the associated mid-sole or other shoe upper to which the outer member is attached. Also, attachment flanges could be disposed along the entire length of the outer member or only along the heel portion thereof, again depending upon the particular type of shoe structure to which the outer member is to be attached.

From the foregoing, it can be seen that there has been described an improved heel and/or sole structure, wherein a generally U-shaped bulge having a bight portion and elongated leg portions tapered in depth and width, with the leg portions spaced apart farther than their maximum width and disposed closer to the peripheral edge of the structure than to the longitudinal axis thereof, so that the bulge provides a lifting and cushioning effect while, at the same, the leg portions thereof provide significantly improved lateral stability.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered byway of illustration only and not as a limitation. The actual scope of the invention is intended to be defined in the following claims when viewed in their proper perspective based on the prior art.

We claim:

1. Shoe sole and/or heel structure comprising: an outer member including a heel portion and/or a metatarsal portion and having an exterior surface and a peripheral edge and a longitudinal axis, and an elongated bulge formed in one of said portions and projecting from said exterior surface and defining an elongated fluid-containing cavity, said bulge having an elongated leg portion disposed closer to the peripheral edge than to the longitudinal axis and extending along the peripheral edge from a first end to a second end, said cavity having a cross-sectional area which tapers from a maximum value at the first end of said leg portion to a minimum value at the second end of said leg portion.

2. The shoe sole and/or heel structure of claim 1, wherein said cavity has a substantially vertical depth in use which tapers from a maximum value at said first end to a minimum value at said second end of said leg portion.

3. The shoe sole and/or heel structure of claim 1, wherein the portion of said cavity defined by said leg portion has a substantially horizontal width in use which tapers from a maximum value at said first end to a minimum value at said second end of said leg portion.

4. The shoe sole and/or heel structure of claim 3, wherein said cavity has a substantially vertical depth in use which tapers from a maximum value at said first end to a minimum value at said second end of said leg portion.

5. The shoe sole and/or heel structure of claim 1, wherein said outer member has an interior surface with said cavity opening at said interior surface, and further comprising a sealing member impermeable to air and fixedly secured to said interior surface for closing and hermetically sealing said cavity, and fluid disposed in said sealed cavity.

6. The shoe sole and/or heel structure of claim 5, wherein said fluid is air at atmospheric pressure.

7. The shoe sole and/or heel structure of claim 1, wherein said bulge is disposed only in a heel portion of said outer member with said first end of said leg portion disposed rearwardly and said second end of said leg portion disposed forwardly of said heel portion.

8. The shoe sole and/or heel structure of claim 1, wherein said bulge is disposed only in a metatarsal portion of said outer member with said first end of said leg portion disposed forwardly and said second end of said leg portion disposed rearwardly.

9. The shoe sole and/or heel structure of claim 8, and further comprising a second elongated bulge molded into a heel portion of said outer member and projecting from said exterior surface and defining an elongated fluid-containing cavity, said second bulge having a leg portion being disposed closely adjacent to the peripheral edge and extending therealong from a first end to a second end, the cavity defined by said second bulge having a cross-sectional area which tapers from a maximum value at the first end of said leg portion of said second bulge to a minimum value at the second end of said leg portion of said second bulge, said first end of said leg portion of said second bulge extending rearwardly and said second end of said leg portion of said second bulge extending forwardly.

10. The shoe sole and/or heel structure of claim 1, wherein said first end of said leg portion of said bulge is disposed in a heel portion of said outer member, said second end of said leg portion of said bulge being disposed in a metatarsal portion of said outer member.

11. The shoe sole and/or heel structure of claim 1, wherein said bulge includes two elongated leg portions respectively extending along opposite sides of said outer member, each of said leg portions being disposed closer to the peripheral edge than to the longitudinal axis and extending along the peripheral edge from a first end to a second end, said cavity having a cross-sectional area which tapers from a maximum value at the first ends of said leg portions to a minimum value at the second ends of said leg portions, each of said leg portions having a width substantially less than the distance therebetween.

12. The shoe sole and/or heel structure of claim 11, wherein said bulge is generally U-shaped.

13. The shoe sole and/or heel structure of claim 11, wherein said cavity has a substantially vertical depth in use which tapers from a maximum value at said first ends to a minimum value at said second ends of said leg portions.

14. Shoe sole and/or heel structure comprising: an outer member including a heel portion and/or a metatarsal portion and having an exterior surface and a peripheral edge and a longitudinal axis, first and second bulges formed in one of said portions and projecting from said exterior surface and respectively defining first and second fluid-containing cavities, said first bulge being generally U-shaped and having a bight portion and two elongated leg portions, each of said leg portions being disposed closer to the peripheral edge than to the longitudinal axis and extending along the peripheral edge from a bight end to a distal end, said first cavity having a cross-sectional area which tapers from a maximum value at the bight ends of said leg portions to a minimum value at the distal ends of said leg portions, each of said leg portions having a width substantially less than the distance therebetween, said second bulge being disposed between said leg portions of said first bulge, and a restricted passageway formed in said outer member and communicating with each of said first and second cavities.

15. The shoe sole and/or heel structure of claim 14, wherein said restricted passageway communicates with said first cavity at the bight portion of said first bulge.

16. The shoe sole and/or heel structure of claim 14, wherein said first and second bulges are disposed only in a heel portion of said outer member.

17. The shoe sole and/or heel structure of claim 14, wherein said first and second bulges are disposed only in a metatarsal portion of said outer member.

18. The shoe sole and/or heel structure of claim 17, and further comprising third and fourth bulges formed in a heel portion of said outer member and projecting from said exterior surface and respectively defining third and fourth elongated fluid-containing cavities, said third bulge being generally U-shaped and having a bight portion and two elongated leg portions, each of said leg portions of said third bulge being disposed closely adjacent to the peripheral edge and extending therealong from a bight end to a distal end, said third cavity having a cross-sectional area which tapers from a maximum value at the bight ends of said leg portions of said third bulge to a minimum value at the distal ends of said leg portions of said third bulge, each of said leg portions of said third bulge having a width substantially less than the distance therebetween, said fourth bulge being disposed between said leg portions of said third bulge, and a second restricted passageway formed in said outer member and communicating with each of said third and fourth cavities.

19. The shoe sole and/or heel structure of claim 14, wherein said second bulge projects from said exterior surface a distance substantially greater than does said first bulge.

20. Shoe sole and/or heel structure comprising: an outer member including a heel portion and/or a metatarsal portion and having an exterior surface and a peripheral edge and a longitudinal axis, and a plurality of bulges formed in said member and projecting from said exterior surface and respectively defining fluid-containing cavities, one of said bulges being generally U-shaped and having a bight portion and two elongated leg portions, each of said leg portions being disposed closer to the peripheral edge than to the longitudinal axis and extending along the peripheral edge from a bight end to a distal end, the cavity defined by said one bulge having a cross-sectional area which tapers from a maximum value at the bight ends of said leg portions to a minimum value at the distal ends of said leg portions, each of said leg portions having a width substantially less than the distance therebetween, the cavity defined by said one bulge being isolated from any other cavity.

21. The shoe sole and/or heel structure of claim 20, wherein said plurality of bulges includes two bulges other than said one bulge.

22. The shoe sole and/or heel structure of claim 21, wherein said two other bulges are respectively disposed in heel and metatarsal portions of said outer member.

23. The shoe sole and/or heel structure of claim 22, and further comprising a restricted passageway formed in said outer member and communicating with each of the cavities defined by said two other bulges.

24. The shoe sole and/or heel structure of claim 20, wherein said one bulge is disposed only in a heel portion of said outer member.

25. The shoe sole and/or heel structure of claim 20, wherein said bight portion is disposed in a heel portion of said outer member, said leg portions extending forwardly from said heel portion and into a metatarsal portion of said outer member.

* * * * *

UNITED STATES PATENT AND TRADEMARK OFFICE
CERTIFICATE OF CORRECTION

PATENT NO. : 5,679,439
DATED : Oct. 21, 1997
INVENTOR(S) : Karl M. Schmidt et al.

It is certified that error appears in the above-indentified patent and that said Letters Patent is hereby corrected as shown below: On the title page, item:

[56] References cited should include the following:

```
--   745,793    12/03   Corman
   1,605,985    11/26   Rasmussen
   1,977,695    10/34   Pinaud
   2,080,499    05/37   Nathansohn
   2,532,742    12/50   Stoiner
   2,863,230    12/58   Cortina
   3,044,190    07/62   Urbany
   4,071,963    02/78   Fukuoka
   4,224,749    09/80   Diaz-Cano
   4,358,902    11/82   Cole et al.
   4,446,634    05/84   Johnson et al.
   4,610,099    09/86   Signori
   4,934,072    06/90   Fredericksen et al.
   4,856,208    08/89   Zaccaro 871,261            Germany
   1,287,477            Germany--.
```

Signed and Sealed this

Twenty-fourth Day of March, 1998

Attest:

BRUCE LEHMAN

*Attesting Officer*   Commissioner of Patents and Trademarks